United States Patent
Sharma

(10) Patent No.: US 11,844,808 B2
(45) Date of Patent: Dec. 19, 2023

(54) METHODS AND COMPOSITIONS FOR TREATING PRE-ECLAMPSIA

(71) Applicant: Women & Infants Hospital of Rhode Island, Providence, RI (US)

(72) Inventor: Surendra Sharma, Warwick, RI (US)

(73) Assignee: Women & Infants Hospital of Rhode Island, Providence, RI (US)

( * ) Notice: Subject to any disclaimer, the term of this patent is extended or adjusted under 35 U.S.C. 154(b) by 825 days.

(21) Appl. No.: 16/961,085

(22) PCT Filed: Jan. 16, 2019

(86) PCT No.: PCT/US2019/013800
§ 371 (c)(1),
(2) Date: Jul. 9, 2020

(87) PCT Pub. No.: WO2019/143685
PCT Pub. Date: Jul. 25, 2019

(65) Prior Publication Data
US 2021/0052617 A1 Feb. 25, 2021

Related U.S. Application Data

(60) Provisional application No. 62/617,909, filed on Jan. 16, 2018.

(51) Int. Cl.
*A61K 31/7016* (2006.01)
*A61P 9/12* (2006.01)
*A61P 15/00* (2006.01)
*G01N 33/68* (2006.01)

(52) U.S. Cl.
CPC .......... *A61K 31/7016* (2013.01); *A61P 9/12* (2018.01); *A61P 15/00* (2018.01); *G01N 33/689* (2013.01); *G01N 2800/368* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2003/0211969 A1* | 11/2003 | Fisher | A61P 7/04 424/94.63 |
| 2014/0141456 A1 | 5/2014 | Kumar et al. | |
| 2014/0315818 A1 | 10/2014 | Newell et al. | |
| 2016/0355826 A1* | 12/2016 | Khvorova | A61K 31/713 |
| 2019/0336518 A1 | 11/2019 | Megiddo | |

FOREIGN PATENT DOCUMENTS

| | | | | |
|---|---|---|---|---|
| WO | WO 2014/181333 A2 | 11/2014 | | |
| WO | WO-2016083623 A1 * | 6/2016 | | A61K 47/48 |

OTHER PUBLICATIONS

International Search Report and Written Opinion, International Patent Application No. PCT/US2019/013800, dated Mar. 14, 2019.
Nakashima, A., et al., "Evidence for Lysosomal Biogenesis Proteome Defect and Impaired Autophagy in Preeclampsia", Autophagy Dec. 26, 2019; 1-15.
Kaplon, R. E., et al., "Oral trehalose supplementation improves resistance artery endothelial function in healthy middle-aged and older adults", Aging, Jun. 2016, vol. 8 No 6.
Chen, H., et al., "Determination of trehalose by ion chromatography and its application to a pharmacokinetic study in rats after intra-muscular injection", Biomedical Chromatography. 2018; e4355, 1-6.
Wada, S., et al., "Novel autophagy inducers lentztrehaloses A, B and C", The Journal of Antibiotics (2015) 68, 521-529.
Zhang, M., et al., "Synthesis and Determination of Absolute Configuration of Lentztrehalose A", Chem. Pharm. Bull. 63, 961-966 (2015).
Wada, S., et al., "Stability and Bioavailability of Lentztrehaloses A, B, and C as Replacements for Trehalose", J Agric Food Chem. Sep. 28, 2016;64(38):7121-6.

* cited by examiner

*Primary Examiner* — Dale R Miller
(74) *Attorney, Agent, or Firm* — Saul Ewing LLP; Brian R. Landry; Justin W. Crotty

(57) ABSTRACT

Methods and compositions using trehalose or a derivative or prodrug thereof for treating pre-eclampsia in a subject are disclosed.

13 Claims, 18 Drawing Sheets

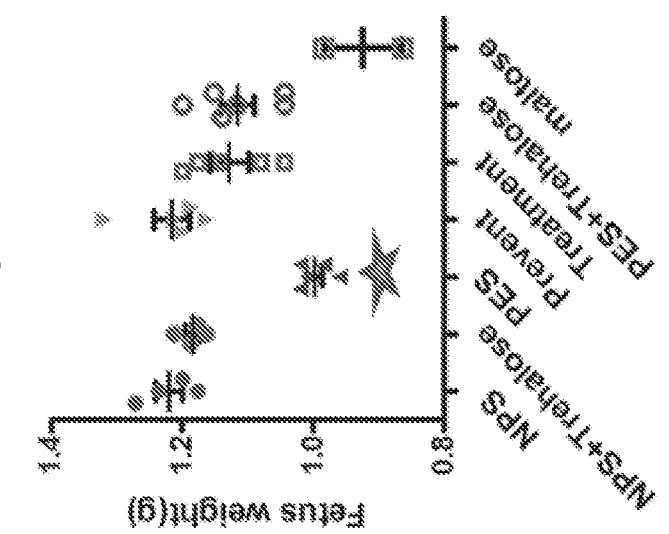
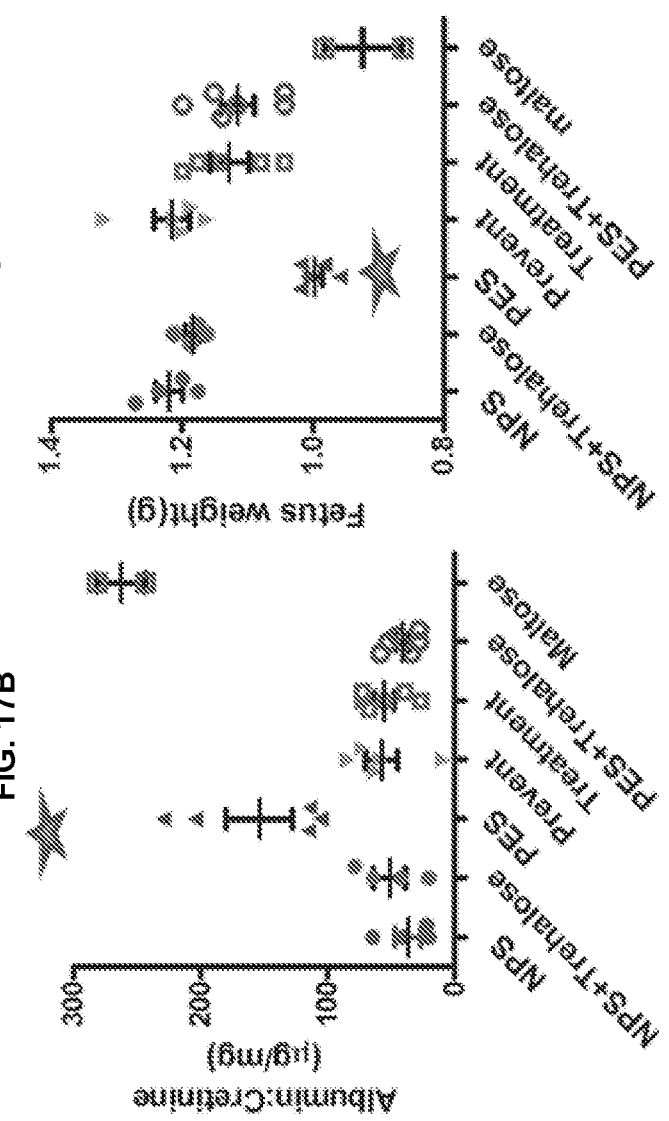
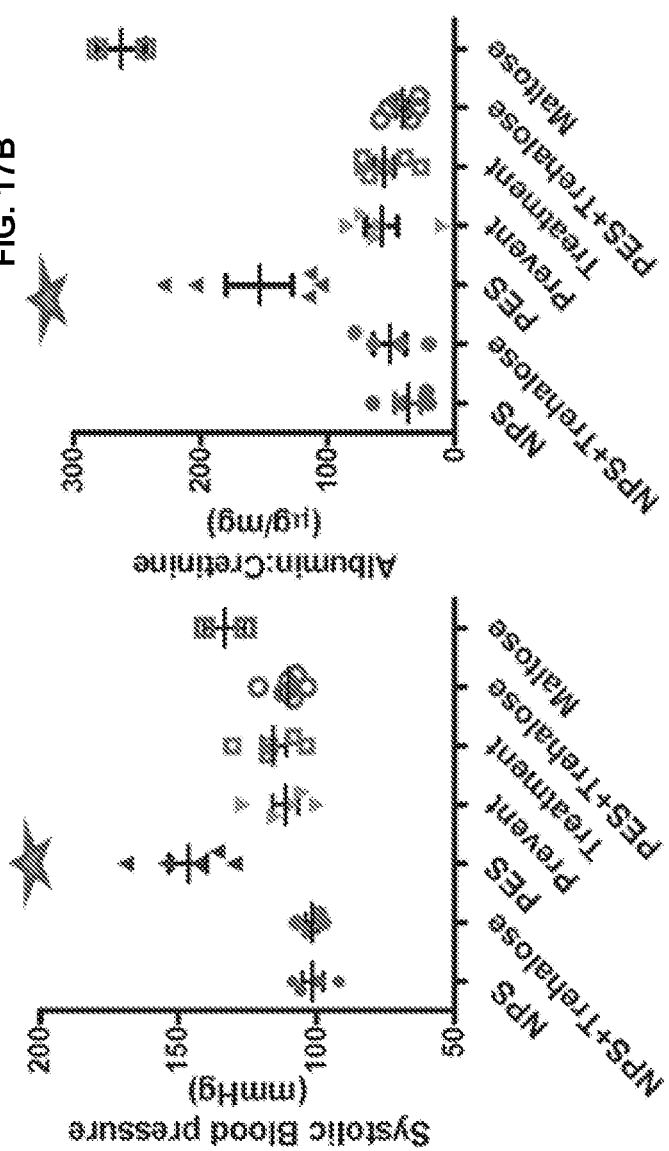
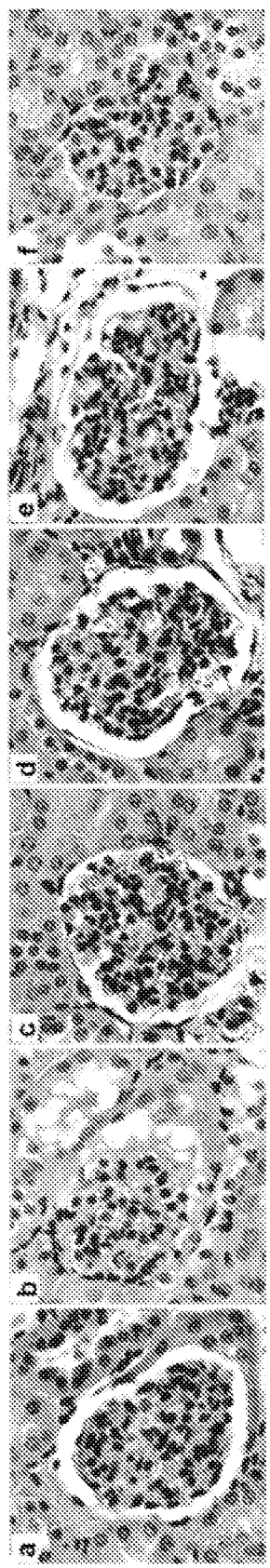
FIG. 17A
FIG. 17B
FIG. 17C
FIG. 17D

METHODS AND COMPOSITIONS FOR TREATING PRE-ECLAMPSIA

CROSS-REFERENCE TO RELATED APPLICATIONS

The present application is a national phase application under 35 U.S.C. § 371 of International Application No. PCT/US2019/013800, filed Jan. 16, 2019, which claims priority under 35 U.S.C. § 119(e) to U.S. Provisional Patent Application Ser. No. 62/617,909, filed Jan. 16, 2018, the contents of which are incorporated herein by reference in its their entirety.

BACKGROUND OF THE INVENTION

Pre-eclampsia is a serious and potentially fatal pregnancy complication affecting 2-8% of pregnancies worldwide. Risk factors include high blood pressure and obesity but the mechanism and cause of the condition are poorly understood.

SUMMARY OF THE INVENTION

The invention is based, at least in part, on the discovery that Chronic Traumatic Encephalothapy (CTE)/Tauopathy-like features are quite distinct in pre-eclampsia placenta and hypoxia-treated human trophoblasts. Further, indication of cis P-Tau and inhibition of Pin1 can be reversed by trehalose in hypoxia-treated primary trophoblasts and a trophoblast cell line.

Thus, in one aspect, the invention provides a method of treating pre-eclampsia in a subject in need thereof, the method comprising administering to the subject a pharmaceutical composition comprising a therapeutically effective amount of trehalose or a derivative or prodrug thereof, thereby treating pre-eclampsia in the subject.

In another aspect, the invention provides a method of preventing or treating pre-eclampsia in a subject in need thereof, the method comprising:
a) detecting a level of at least one tauopathy marker in a sample obtained from the subject,
b) comparing the level of the at least one tauopathy marker to a corresponding reference level; and
wherein if the level of the at least one tauopathy marker is different from the corresponding reference level,
c) administering to the subject a pharmaceutical composition comprising a therapeutically effective amount of trehalose or a derivative or prodrug thereof, thereby treating or preventing pre-eclampsia in the subject.

In one embodiment, the methods further comprise obtaining the sample from the subject. In another embodiment, the sample is selected from the group consisting of a serum sample, a urine sample and a sample obtained from the placenta. In yet another embodiment, the sample is a serum or urine sample. In still another embodiment, the at least one tauopathy marker is selected from the group consisting of a protein aggregate, cis p-tau and combinations thereof.

In embodiments of the aforementioned aspects of the invention, the pre-eclampsia is characterized by elevated levels of cis-p-tau in a sample from the subject. In other embodiments, the pre-eclampsia is characterized by depressed levels and/or inactivation of Pin-1 in a sample from the subject. In yet other embodiments, the pre-eclampsia is characterized by the presence of protein aggregates in a sample taken from the subject. In still other embodiments, the trehalose promotes degradation of protein aggregates. In particular embodiments, the sample taken from the subject is a serum sample or a urine sample.

In embodiments of the aforementioned aspects of the invention, the subject is a mammal. In certain embodiments, the subject is a human female. In certain embodiments, the human female is characterized by a risk factor selected from the group consisting of previous history of pre-eclampsia, multiple gestation, history of chronic high blood pressure, history of diabetes, history of kidney disease, history of organ transplant, first pregnancy, obesity and combinations thereof.

In other embodiments of the methods of the invention, the method further comprising obtaining trehalose or a derivative or prodrug thereof.

In yet another aspect, the invention provides a kit comprising a pharmaceutical composition comprising a therapeutically effective amount of trehalose or a derivative or prodrug thereof and a pharmaceutically acceptable carrier therefor and instructional material for use for the prevention or treatment of pre-eclampsia.

BRIEF DESCRIPTION OF THE DRAWINGS

For a fuller understanding of the invention, reference is made to the following detailed description taken in conjunction with the accompanying figures.

FIGS. 17A-17D show that trehalose inhibits preeclampsia-like features in pregnant mice.

DEFINITIONS

Figure 1:
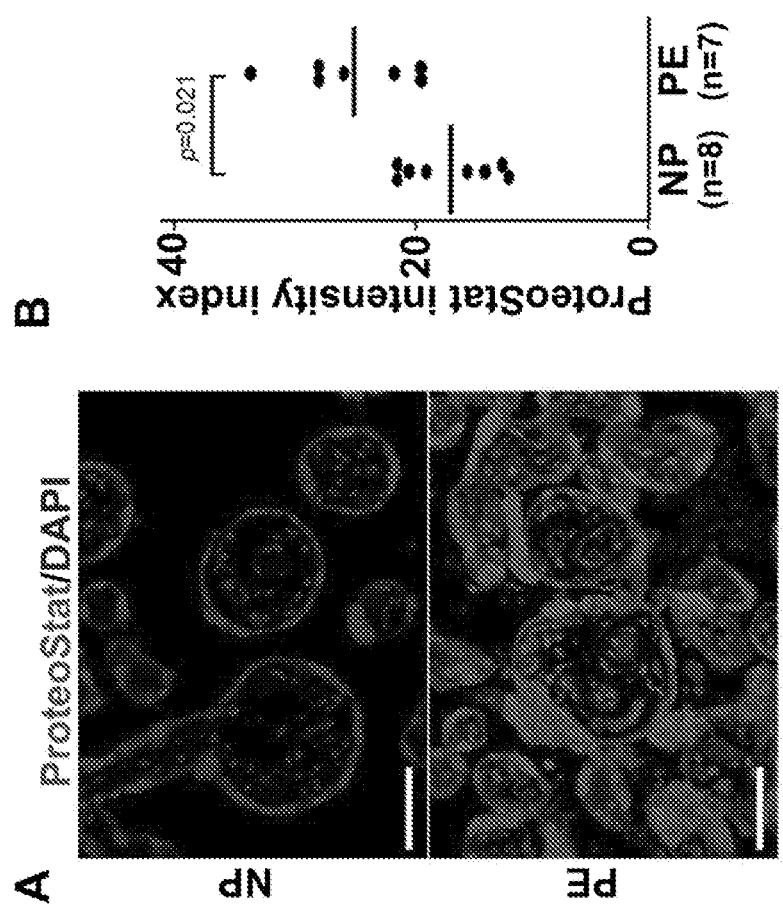
FIGS. 1A and 1B depict the detection of protein aggregates in pre-eclampsia (PE) placenta by ProteoStat® staining.

The instant invention is more clearly understood with reference to the following definitions:

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application. For example, it should be understood that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The term "obtaining" as in "obtaining trehalose or a derivative or prodrug thereof" refers to synthesizing, purchasing, or otherwise acquiring trehalose or a derivative or prodrug thereof.

"Biological sample" or "sample" as used herein means a biological material isolated from an individual. The biological sample may contain any biological material suitable for detecting the desired biomarkers, and may comprise cellular and/or non-cellular material obtained from the individual. A biological sample may be of any biological tissue or fluid. Frequently the sample will be a "clinical sample" which is a sample derived from a patient. Typical clinical samples include, but are not limited to, bodily fluid samples such as synovial fluid, sputum, blood, urine, blood plasma, blood serum, sweat, mucous, saliva, lymph, bronchial aspirates, peritoneal fluid, cerebrospinal fluid, and pleural fluid, and tissues samples such as blood-cells (e.g., white cells), tissue or fine needle biopsy samples and abscesses or cells therefrom. Biological samples may also include sections of tissues, such as frozen sections or formalin fixed sections taken for histological purposes.

The terms "biomarker" or "marker," as used herein, refers to a molecule that can be detected. Therefore, a biomarker according to the present invention includes, but is not limited to, a nucleic acid, a polypeptide, a carbohydrate, a lipid, an inorganic molecule, an organic molecule, each of which may vary widely in size and properties. A "biomarker" can be a bodily substance relating to a bodily condition or disease. A "biomarker" can be detected using any means known in the art or by a previously unknown means that only becomes apparent upon consideration of the marker by the skilled artisan.

The term "biomarker (or marker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein. Measuring a biomarker also includes reverse transcription of RNA into cDNA (i.e. for reverse transcription-qPCR measurement of RNA levels.).

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. As defined by the Food and Drug Administration (FDA), a biomarker is a characteristic (e.g., measurable DNA and/or RNA and protein) that is "objectively measured and evaluated as an indicator of normal biologic processes, pathogenic processes, or pharmacologic responses to a therapeutic intervention or other interventions". Biomarkers also include any calculated indices created mathematically or combinations of any one or more of the foregoing measurements, including temporal trends and differences.

The term "prodrug" refers to a derivatized form of a drug molecule that, while in certain embodiments not pharmacologically active itself, is chemically or enzymatically altered in the body to produce one or more active forms of the drug. A prodrug can in other embodiments be pharmacologically active, but can be chemically or enzymatically altered in the body to produce a more active form or a form with different pharmacological activity.

As used herein, "tau" refers to a protein that is the product of alternative splicing from a single gene that in humans is designated MAPT (microtubule-associated protein tau) and is located on chromosome 17.

A "tauopathy marker" as used herein, is a biomarker for dysregulation of tau that results in protein aggregation causing pre-eclampsia. In various embodiments, biomarkers in the context of the present invention include: PIN1 (peptidylprolyl cis/trans isomerase, NIMA-interacting 1), a gene that encodes Pin1, one of two peptidyl-prolyl cis/trans isomerases (PPIases) that catalyze the cis/trans isomerization of peptidyl-prolyl peptide bonds; cis p-tau (cis phosphorylated tau), one of two conformations of tau that are regulated by Pin1; and protein aggregates.

As used herein, a "derivative" is a compound that can be imagined to arise or actually be synthesized from a parent compound by replacement of one atom with another atom or group of atoms while preserving the function of the parent compound. In particular, derivatives encompass functional analogs of the parent compound that share similar chemical structures with the chemical structure of the parent compound and exhibit the same or similar physical, chemical, biochemical, or pharmacological properties. In various embodiments, the trehalose derivative can be lentztrehalose.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The "level" of one or more biomarkers means the absolute or relative amount or concentration of the biomarker in the sample as determined by measuring mRNA, cDNA or protein, or any portion thereof such as oligonucleotide or peptide.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Protein aggregation" and "protein aggregate" as used herein are interchangeable and refer to a biological phenomenon in which mis-folded proteins aggregate (i.e., accumulate and clump together) either intra- or extracellularly. Such protein aggregates include but are not limited to amyloid, which is an extracellular, proteinaceous deposit exhibiting beta sheet structure that can be identified by apple-green birefringence when stained with congo red and seen under polarized light.

A "reference level" of a biomarker means a level of the biomarker that is indicative of the absence of a particular disease state (e.g., pre-eclampsia) or phenotype (normal levels of Pin1). When the level of a biomarker in a subject is different from the reference level of the biomarker it is indicative of the presence of a particular disease state or phenotype. When the level of a biomarker in a subject is within the reference level of the biomarker it is indicative of a lack of a particular disease state or phenotype.

The phrase "therapeutically effective amount," or "effective amount" as used herein, refer to an amount that is sufficient or effective to prevent or treat (delay or prevent the onset of, prevent the progression of, inhibit, decrease or reverse) a disease or condition associated with pre-eclampsia, including alleviating symptoms of such diseases.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Figure 4:
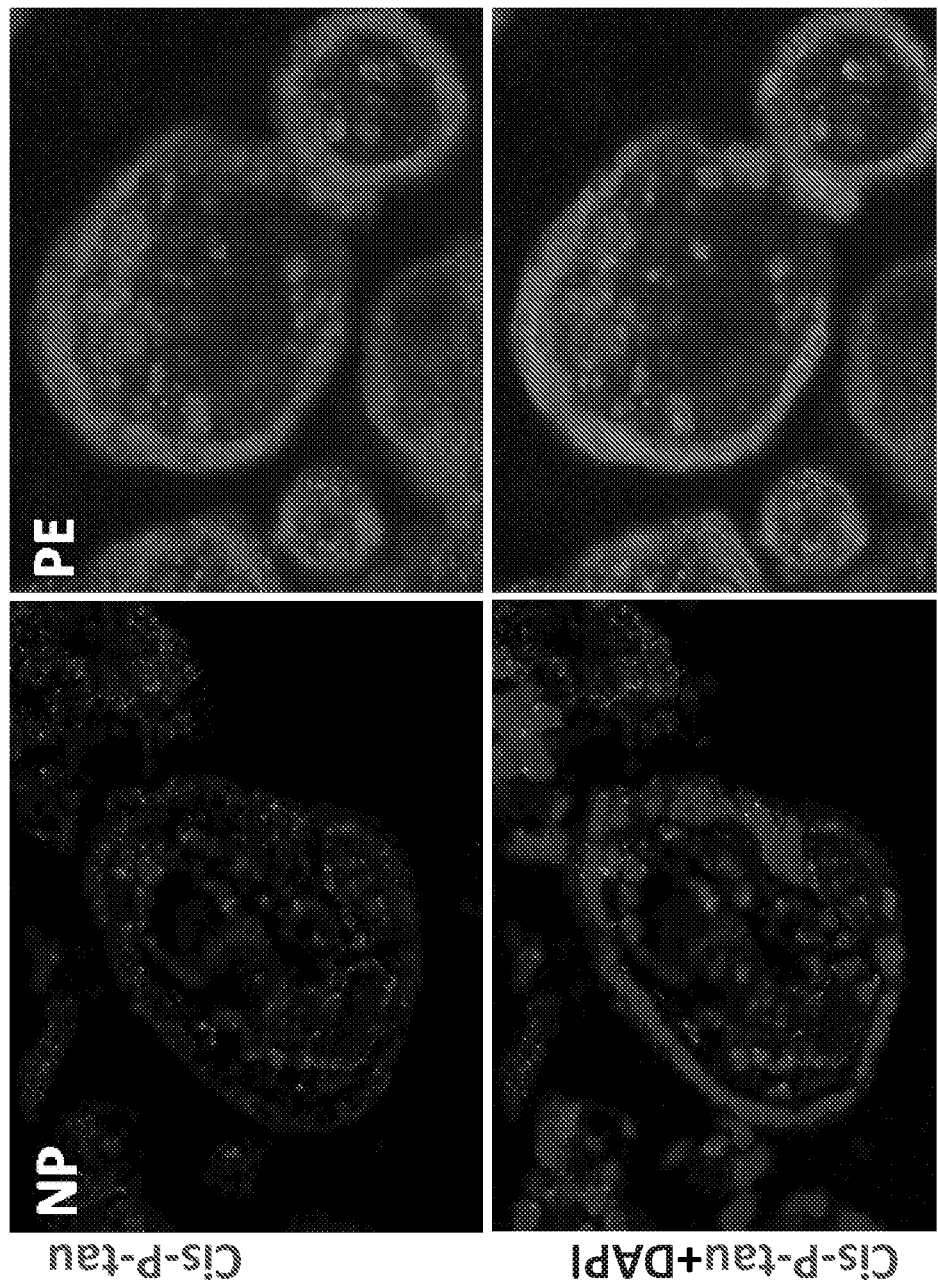
FIG. 4 depicts cis-p-tau expression in the placentas from normal pregnancy (NP) and pre-eclampsia (PE).
Figure 5:
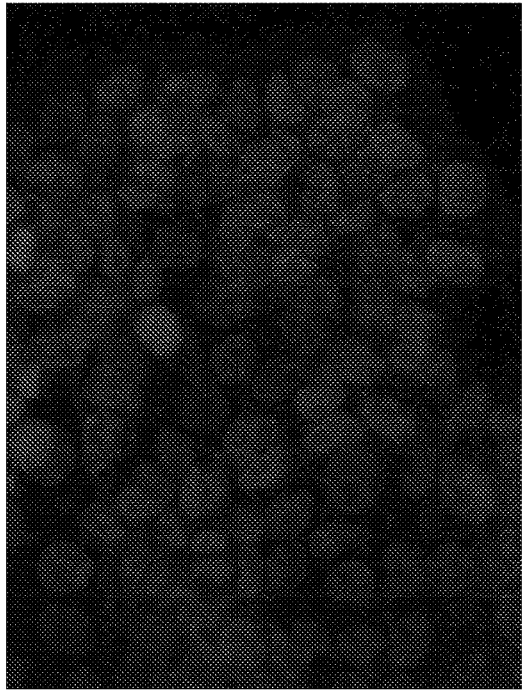
FIG. 5 depicts cis-p-tau expression in normoxia/hypoxia-treated TCL-1 cells.
Figure 5:
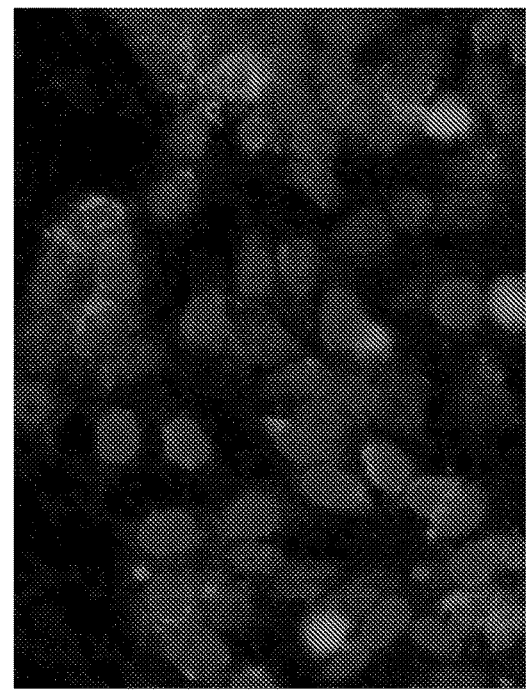
Figure 5:
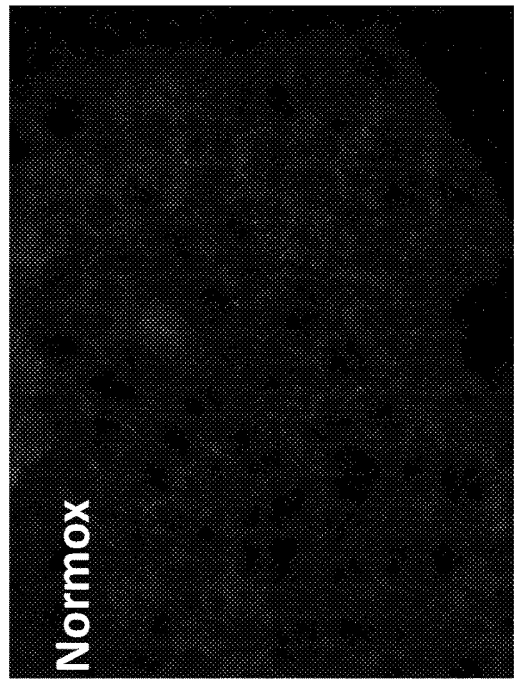
Figure 6:
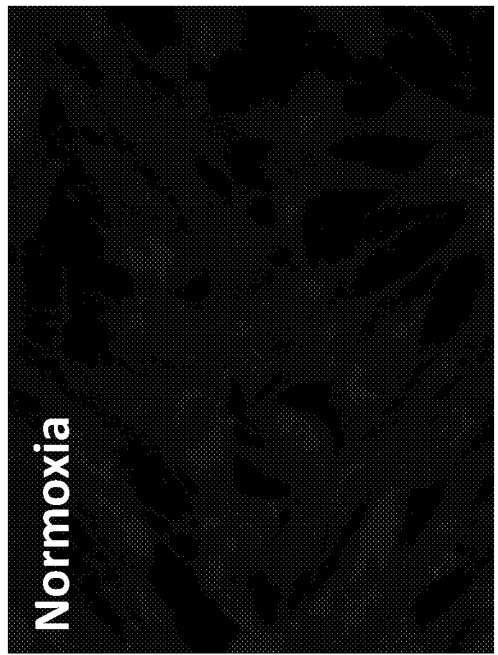
FIG. 6 depicts cis-p-tau expression in normoxia/hypoxia-treated primary trophoblasts.
Figure 6:
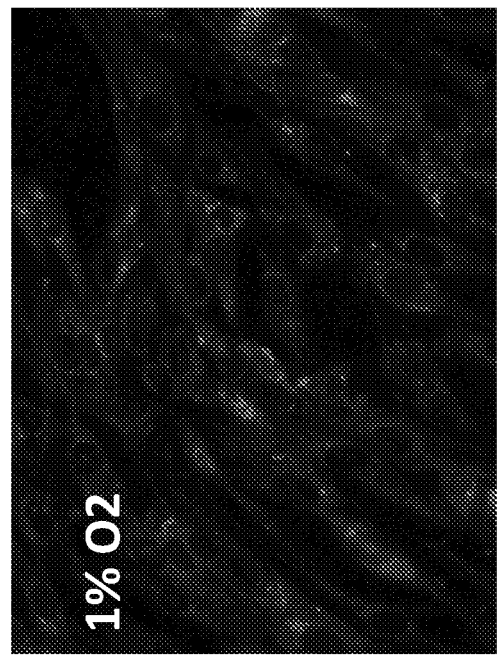
Figure 6:
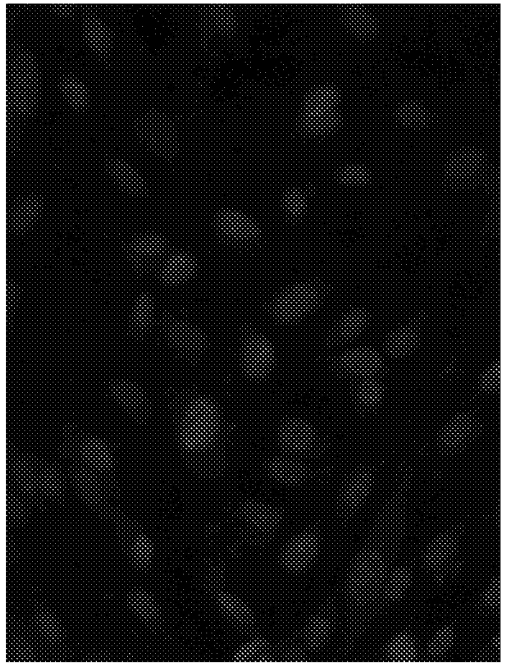
Figure 6:
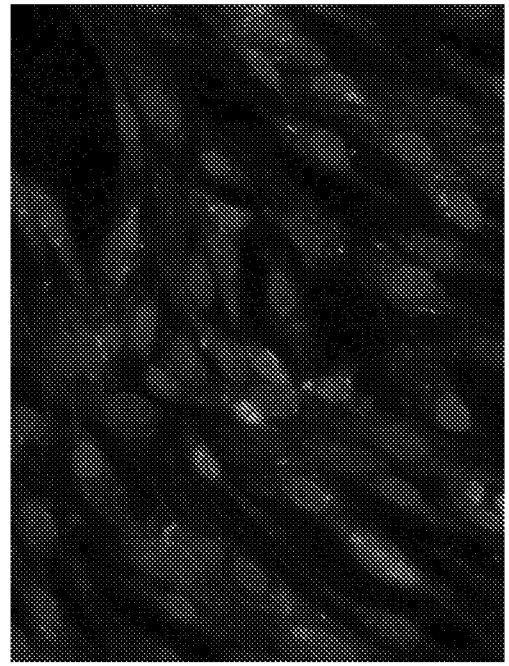
Figure 7:
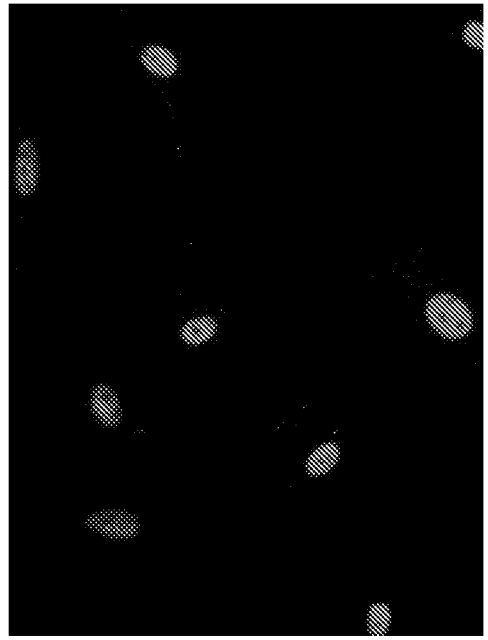
FIG. 7 depicts trans-p-tau expression in normoxia/hypoxia-treated primary trophoblasts.
Figure 7:
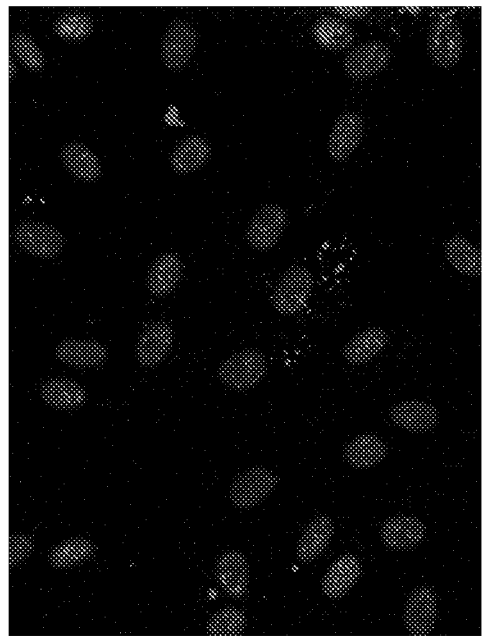
Figure 7:
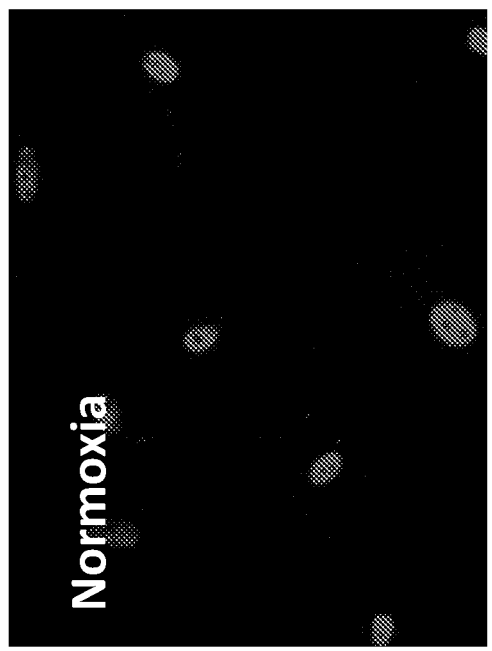
Figure 7:
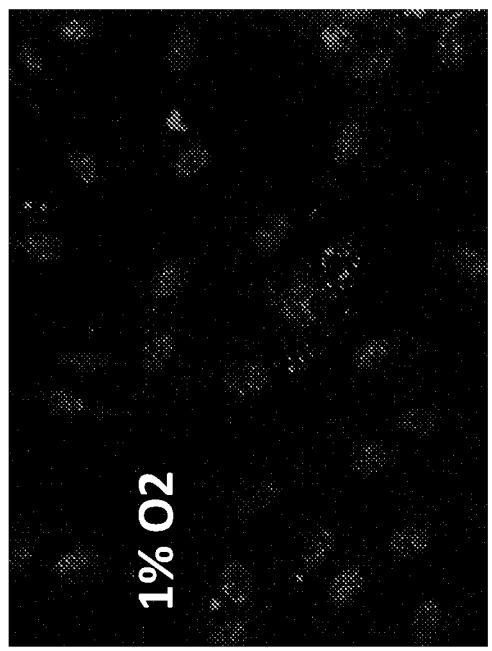

Without wishing to be limited by theory, the invention is based in part on the discovery that protein aggregation plays a role in the pathology of pre-eclampsia and the invention of methods for treating pre-eclampsia by targeting protein aggregates and mechanisms by which protein aggregates form. FIGS. 1A and 1B show the presence of protein aggregates in the placentas of women suffering from pre-eclampsia. FIGS. 4-6 indicate a link between cis-p-tau, which is associated with protein aggregation, and pre-eclampsia.

Methods of Treating Pre-Eclampsia

In one aspect the invention provides a method of treating pre-eclampsia in a subject in need thereof, the method comprising administering to the subject a pharmaceutical composition comprising a therapeutically effective amount of trehalose or a derivative or prodrug thereof, thereby treating pre-eclampsia in the subject. Appropriate pharmaceutical compositions and carriers are described below.

Based on the disclosure herein, a person of skill in the art would be able to detect pre-eclampsia prior to the onset of symptoms and then deliver treatment with trehalose. Accordingly, in another aspect, the invention provides a method of preventing or treating pre-eclampsia in a subject in need thereof, the method comprising detecting a level of at least one tauopathy marker in a sample obtained from the subject, comparing the level of the at least one tauopathy marker to a corresponding reference level and wherein if the level of the at least one tauopathy marker is different from the corresponding reference level, administering to the subject a pharmaceutical composition comprising a therapeutically effective amount of trehalose or a derivative or prodrug thereof, thereby treating or preventing pre-eclampsia in the subject. In various embodiments, the tauopathy marker can be cis-p-tau or protein aggregates. In various embodiments, the tauopathy marker can be detected using an antibody. Antibodies for the detection of protein aggregates are commercially available. Antibodies for the detection of cis-p-tau are described in the following References: 1. Nakamura, K., Greenwood, A., Binder, L., Bigio, E. H., Denial, S. J., Nicholson, L., Zhou, X. Z. & Lu, K. P. Proline isomer-specific antibodies reveal the early pathogenic tau conformation in Alzheimer's disease. Cell 149, 232-244 (2012). 2. Kondo, A., Shahpasand, K., Mannix, R., Qiu, J., Moncaster, J., Chen, C. H., Yao, Y., Lin, Y. M., Driver, J. A., Sun, Y., Wei, S., Luo, M., Albayram, O., Huang, P., Rotenberg, R., Ryo, A., Goldstein, L. E., Pascual-Leone, A., Mckee, A., Meehan, W., Zhou, X. Z. & Lu, K. P. Antibody against early driver of neurodegeneration cis P-tau blocks brain injury and tauopathy. Nature 523, 431-436 (2015).

In various embodiments, the method includes a step of obtaining the sample from the subject. In various embodiments the sample is a serum sample, a urine sample or a sample obtained from the placenta of the subject. In various embodiments, the sample is a serum or urine sample.

In various embodiments, the at least one tauopathy marker is a protein aggregate or is cis p-tau. As discussed above, the data presented herein shows that pre-eclampsia can be characterized by elevated levels of cis-p-tau in the sample from the subject which leads to protein aggregation.

Pin-1 is a unique phospho-specific proline known to isomerize cis-p-tau to the benign trans isomer. Deficiencies in the level or activity of Pin-1 may lead to elevated levels of cis-p-tau. Accordingly, in various embodiments, the pre-eclampsia is characterized by depressed levels and/or inactivation of Pin-1.

As shown in FIGS. 8, 9, 10 and 12, an effective amount of trehalose can be used to treat pre-eclampsia. Without wishing to be limited by theory, trehalose may promote the degradation of protein aggregates, thereby preventing or treating pre-eclampsia. Accordingly, in various embodiments, the trehalose promotes the degradation of protein aggregates.

A skilled person will recognize that the subject is not particularly limited and can be any subject in need of treatment for pre-eclampsia. In various embodiments, the subject is a human female. In various embodiments, the human female is characterized by a risk factor selected from the group consisting of previous history of pre-eclampsia, multiple gestation, history of chronic high blood pressure, history of diabetes, history of kidney disease, history of organ transplant, first pregnancy and obesity. In various embodiments, trehalose is administered at a dose of 25-50 µg/ml or at a dose of about 2 g/kg, based on the weight of the subject.

Kits

In another aspect, the invention provides a kit comprising a pharmaceutical composition comprising a therapeutically effective amount of trehalose or a derivative or prodrug thereof and a pharmaceutically acceptable carrier therefor and instructions for use for the prevention or treatment of pre-eclampsia. In various embodiments the kit contains reagents for detecting the level of at least one tauopathy marker and written material and/or reagents for comparing the level of the at least on tauopathy marker to a corresponding reference level. The kit facilitates the treatment and/or detection of pre-eclampsia in settings where it may otherwise be difficult. In various embodiments, the kit contains one of more pharmaceutical compositions comprising trehalose at a dose of 25-50 µg/ml or at a dose of about 2 g/kg, based on the weight of the subject.

Compounds of the Invention

Trehalose, derivatives and prodrugs thereof are useful in the methods of the invention. Trehalose is a very stable disaccharide (two d-glucose molecules) having the following structure:

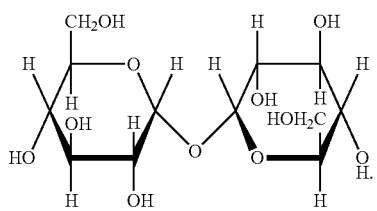

Trehalose is naturally found in over 80 organisms including yeast, bacteria, plants, fungi and invertebrates. Although trehalose has never been identified in mammals, trehalase, the enzyme that degrades trehalose, has been found in the small intestine and other organs of some species. Trehalose is thought to protect the integrity of cells against stresses such as heat, cold, dehydration and oxidation by preventing denaturation of proteins Trehalose is not a substantial part of the modern diet, but is naturally present in honey, brewers and baker's yeast, mushrooms, lobster, and crab. Trehalose is generally regarded as safe by the FDA based on numerous safety studies in mice, rats, and rabbits including in pregnancy. It has been used as a preservative in the food industry, and in pharmaceuticals for the preservation of labile protein drugs. In various embodiments, the methods of the invention employ a trehalose derivative. In various embodiments, the trehalose derivative is lentztrehalose. In various embodiments, the trehalose derivative is trehalose hexaacetate.

Diagnosis

In certain embodiments, the methods for treatment or prevention in accordance with the invention can include a diagnostic regimen. The diagnostic regimen includes the steps of a) detecting a level of at least one tauopathy marker in a sample obtained from the subject; and b) comparing the level of the at least one tauopathy marker to a corresponding reference level.

If the level of the at least one tauopathy marker is different from the corresponding reference level, then administration to the subject a pharmaceutical composition comprising a therapeutically effective amount of trehalose or a derivative or prodrug thereof is indicated.

Administration/Dosage/Formulations

The regimen of administration may affect what constitutes an effective amount. The therapeutic formulations may be administered to the subject either prior to or after the onset of a pre-eclampsia or as a prophylactic. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

An effective amount of the therapeutic compound necessary to achieve a therapeutic effect may vary according to factors such as the state of the disease or disorder in the patient; the age, sex, and weight of the patient; and the ability of the therapeutic compound to treat pre-eclampsia in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of pre-eclampsia in a patient.

The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 350 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of pre-eclampsia in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The present invention also includes a multi-layer tablet comprising a layer providing for the delayed release of one or more compounds of the invention, and a further layer providing for the immediate release of a medication for treatment of certain diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Application Publication Nos. 2003/0147952; 2003/0104062; 2003/0104053; 2003/0044466; 2003/0039688; and 2002/0051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention can be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient and the current medical condition of the patient. The skilled artisan is able to determine appropriate dosages depending on these and other factors.

A suitable dose of a compound of the present invention can be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses. In various embodiments, the dose is 2 about mg/kg, based on the weight of the subject.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between the clinically effective dose and the maximum tolerable dose (MTD) or the side effect inducing dose. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

EXEMPLIFICATION

The following examples are set forth so as to provide those of skill in the art with a complete disclosure and description of how to make and use the therapeutic methods and compositions of the invention, and are not intended to limit the scope of what the inventors regard as their invention.

Example 1: Detection of Protein and TTR Aggregates

Paraffin-embedded sections of placental tissues from term-matched normal pregnant and pre-eclamptic women were de-paraffinized and then treated with 0.1% Sudan Black B for 20 min at room temperature. Tissue sections were then fixed with 4% formaldehyde in PBS for 15 min at 37° C. After washes in deionized water, the sections were stained with ProteoStat® dye (Enzo Life Sciences) for 5 min at room temperature. ProteoStat is a molecular rotor dye that fluoresces when bound to aggregated proteins. Sections were then mounted in anti-quench mounting medium with DAPI. As shown in FIG. 1, a higher level of protein aggregates was detected in the trophoblast layer of the placentas from pre-eclamptic women vs. normal pregnancy controls.

Figure 2:
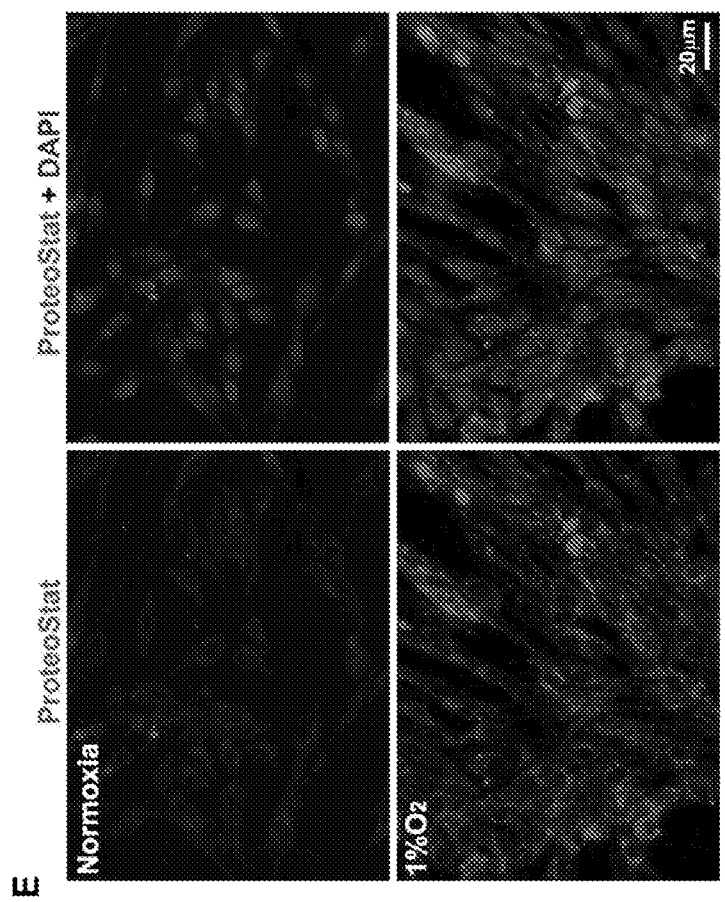
FIG. 2 depicts the detection of protein aggregates in hypoxia-treated primary Trophoblasts by ProteoStat® staining.

Human primary trophoblast cells (ScienCell Research Laboratories) were plated on glass coverslips and cultured in trophoblast medium supplemented with 5% fetal bovine serum, 1% trophoblast growth supplement and 1% penicillin/streptomycin (ScienCell Research Laboratories) in a humidified atmosphere with 5% CO2 at 37° C. Cells were washed three times with Dulbecco's phosphate-buffered saline and cultured in serum-free trophoblast medium prior to exposure to low oxygen tension (1% $O_2$) or normoxia (20% $O_2$) for 3 days. Cells were fixed with 4% formaldehyde in PBS for 15 min, permeabilized and then stained with ProteoStat® dye. As shown in FIG. 2, nuclei were stained with DAPI. Hypoxia-treated cells exhibited high levels of protein aggregates as compared to normoxia-treated cells.

Figure 3:
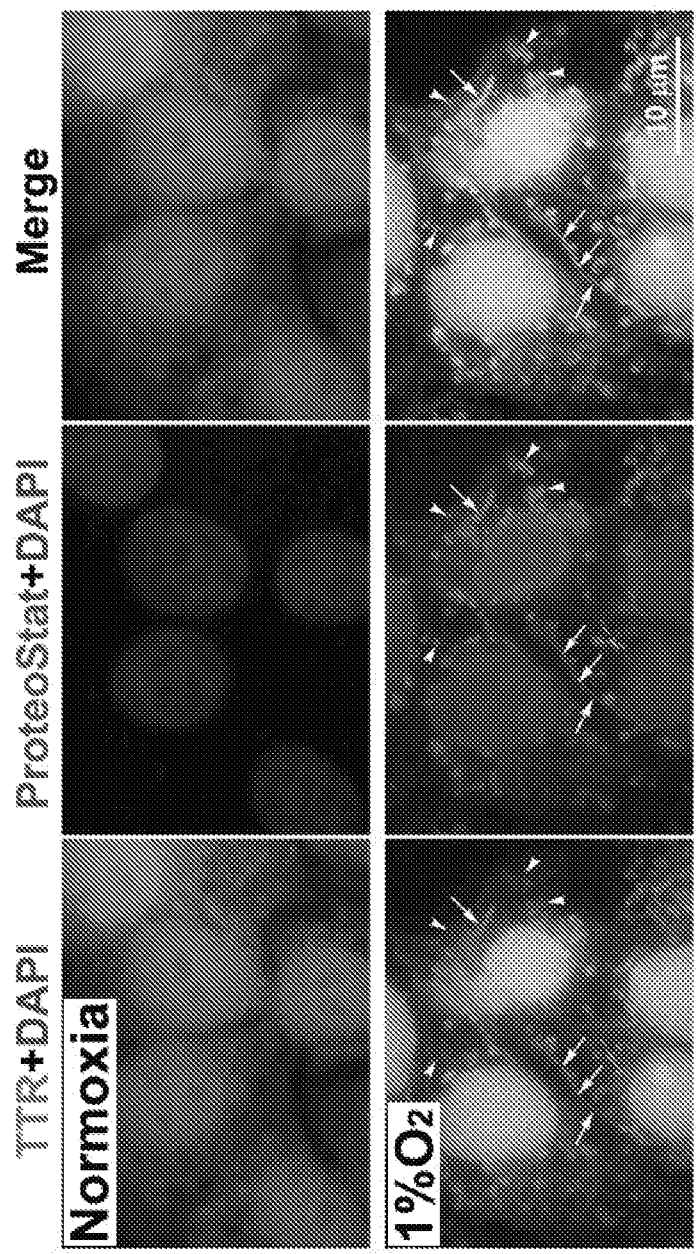
FIG. 3 depicts detection of protein and transthyretin (TTR) aggregates in placenta and trophoblast cells and shows how hypoxia induces TTR aggregation in human trophoblasts.

Paraffin-embedded sections of placental tissues from term-matched normal pregnant and pre-eclamptic women were de-paraffinized, processed for antigen unmasking and then incubated with 0.1% Sudan Black B for 20 min at room temperature. Tissue sections were then fixed with 4% formaldehyde in PBS for 15 min. After washes in deionized water, the sections were stained with ProteoStat® dye for 5 min at room temperature. After several washes, sections were blocked in 0.1% Triton-X/5% BSA/PBS, immunostained overnight at 4° C. for TTR with rabbit anti-human TTR antibody (Dako), and then incubated for 1 h with Alexa Fluor 488 goat anti-rabbit (Thermofisher) at room temperature. Pre-eclamptic placentas showed higher levels of TTR aggregates in the trophoblast layer of villus as compared to normal pregnancy controls. A similar procedure was used to detect TTR aggregates in a cellular model of hypoxia-induced ER stress using human primary villous trophoblast cells. Briefly, TCL-1 cells were plated on glass coverslips and cultured in RPMI medium (Invitrogen) containing 10% fetal bovine serum (Sigma), 100 U/ml penicillin and 100 µg/ml streptomycin (Sigma) in a humidified atmosphere with 5% CO2 at 37° C. Cells were washed three times with Dulbecco's phosphate-buffered saline and cultured in serum-free RPMI medium prior to exposure to low oxygen tension (1% 02) or normoxia (20% 02) for 3 days. Cells were fixed with 4% formaldehyde in PBS for 15 min, blocked in 0.1% Triton-X/3% BSA/PBS, and then immunostained overnight at 4° C. for TTR with rabbit anti-human TTR antibody (Dako). TTR immunoreactivity and nuclei were visualized with Alexa Fluor 488 goat anti-rabbit secondary antibody (Thermofisher) and DAPI, respectively. TTR immunoreactive signal (in green) that co-localized with ProteoStat dye (in red) was indicative of TTR aggregates (in yellow). As shown in FIG. 3 a larger amount of TTR aggregates was detected in the cytoplasm of hypoxia-treated cells relative to normoxia-treated cells.

Example 2: Cis P-Tau and Trans P-Tau Expression

Paraffin-embedded sections of placental tissues from term-matched normal pregnant and pre-eclamptic women were de-paraffinized, processed for antigen unmasking and then incubated with 0.1% Sudan Black B for 20 min at room temperature. After washes in PBS, sections were blocked in 0.1% Triton-X/3% BSA/PBS, immunostained overnight at 4° C. for cis-P-tau with mouse anti-cis-P-tau antibody, and then incubated for 1 h with Alexa Fluor 594 goat anti-mouse secondary antibody at room temperature. Has shown in FIG. 4, high levels of cis-P-tau immunoreactivity were detected in the trophoblast layer of villus of placenta from pre-eclamptic women but not normal pregnant women.

TCL-1 or primary trophoblast cells were grown in serum-free medium and exposed to low oxygen tension (1% $O_2$) or normoxia (20% $O_2$) for 3 days. Cells were fixed, permeabilized and blocked in PBS solution containing 1% Triton-X, 3% BSA and normal donkey serum for 30 min. Cells were incubated with mouse anti-cis-P-tau/anti-trans-P-tau antibody and then with Alexa Fluor 594 donkey anti-mouse secondary antibody for detection of cis-P-tau/trans-P-tau expression. As shown in FIG. 5, low oxygen tension up-regulated the expression of cis-P-tau in the cytoplasm of both TCL-1 and primary trophoblast cells, but decreased trans-P-tau expression in the nuclei of primary trophoblast cells.

Figure 8:
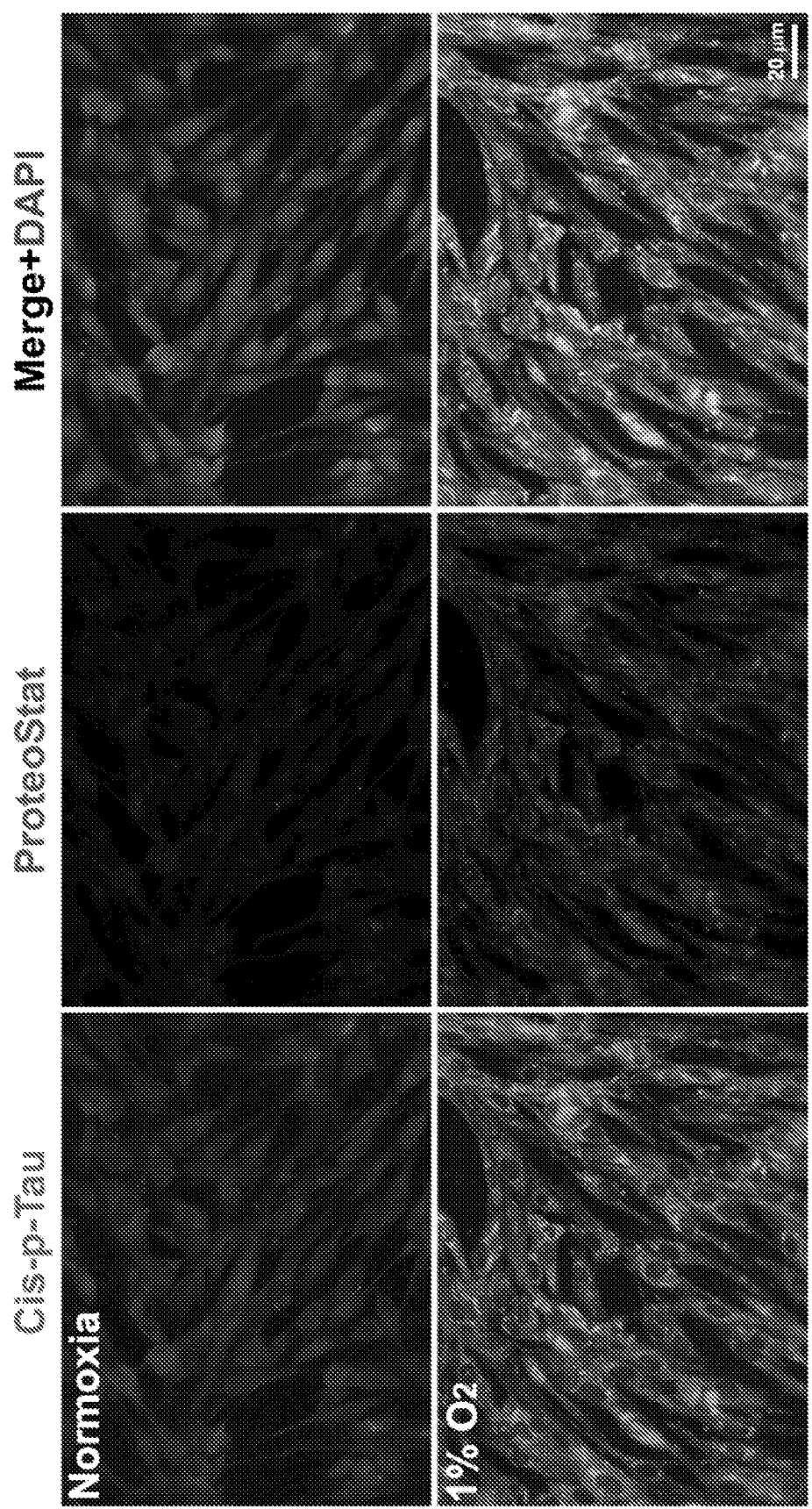
FIG. 8 depicts cis P-tau co-localization with ProteoStat signal evidencing cis P-tau aggregation.

Example 3: Evidence of Cis P-Tau Aggregation—Co-Localization of Cis P-Tau with ProteoStat Signal Primary trophoblast cells were grown in serum-free medium and exposed to low oxygen tension (1% $O_2$) or normoxia (20% $O_2$) for 3 days. Cells were fixed, permeabilized and blocked in PBS solution containing 1% Triton-X, 3% BSA and normal donkey serum for 30 min. Cells were incubated with mouse anti-cis-P-tau antibody and then with Alexa Fluor 488 donkey anti-mouse secondary antibody. After serval washes, cells were stained with ProteoStat® dye for 20 min and mounted in anti-quench mounting medium with DAPI (Vector Laboratories, Inc., Burlingame, CA). As shown in FIG. 8, robust cis-P-tau immunoreactivity colocalized with ProteoStat® dye were detected in hypoxia-treated cells but not normoxia-treated cells, suggesting that hypoxia induces cis-P-tau aggregation.

Example 4: Trehalose Inhibits Cis P-Tau Expression in Primary Trophoblasts

Figure 9:
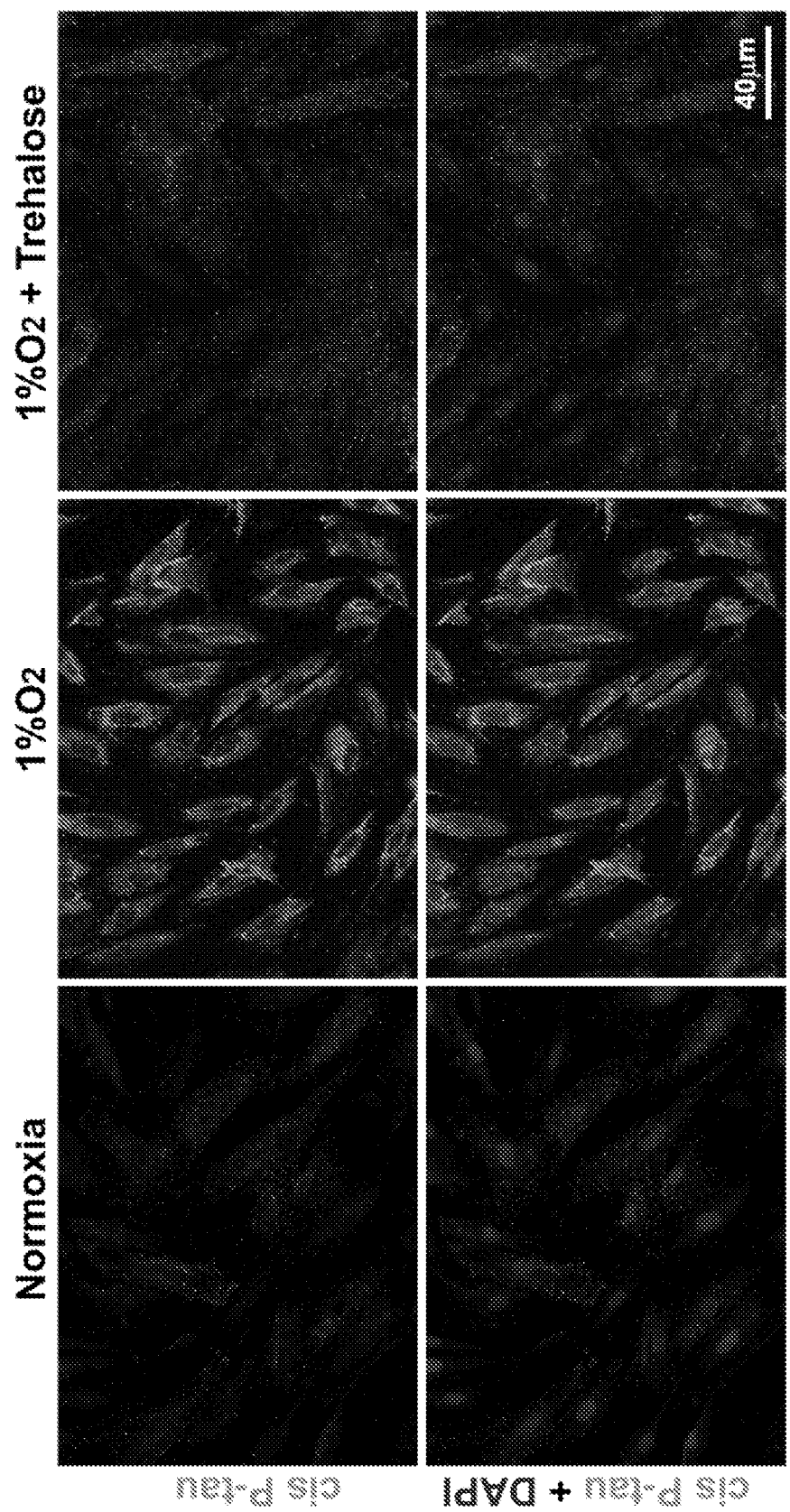
FIG. 9 depicts how hypoxia increases cis-p-tau expression and blockade by trehalose treatment in primary trophoblasts.

Primary trophoblast cells were treated with vehicle or trehalose (50 mM), exposed to low oxygen tension (1% $O_2$) or normoxia, and fixed at 3 days. After permeabilized and blocked in PBS solution containing 1% Triton-X, 3% BSA and normal donkey serum for 30 min, cells were immunostained for cis-P-tau and mounted in anti-quench mounting medium with DAPI. As shown in FIG. 9, trehalose blocked hypoxia-induced upregulation of cis-P-tau.

Figure 10:
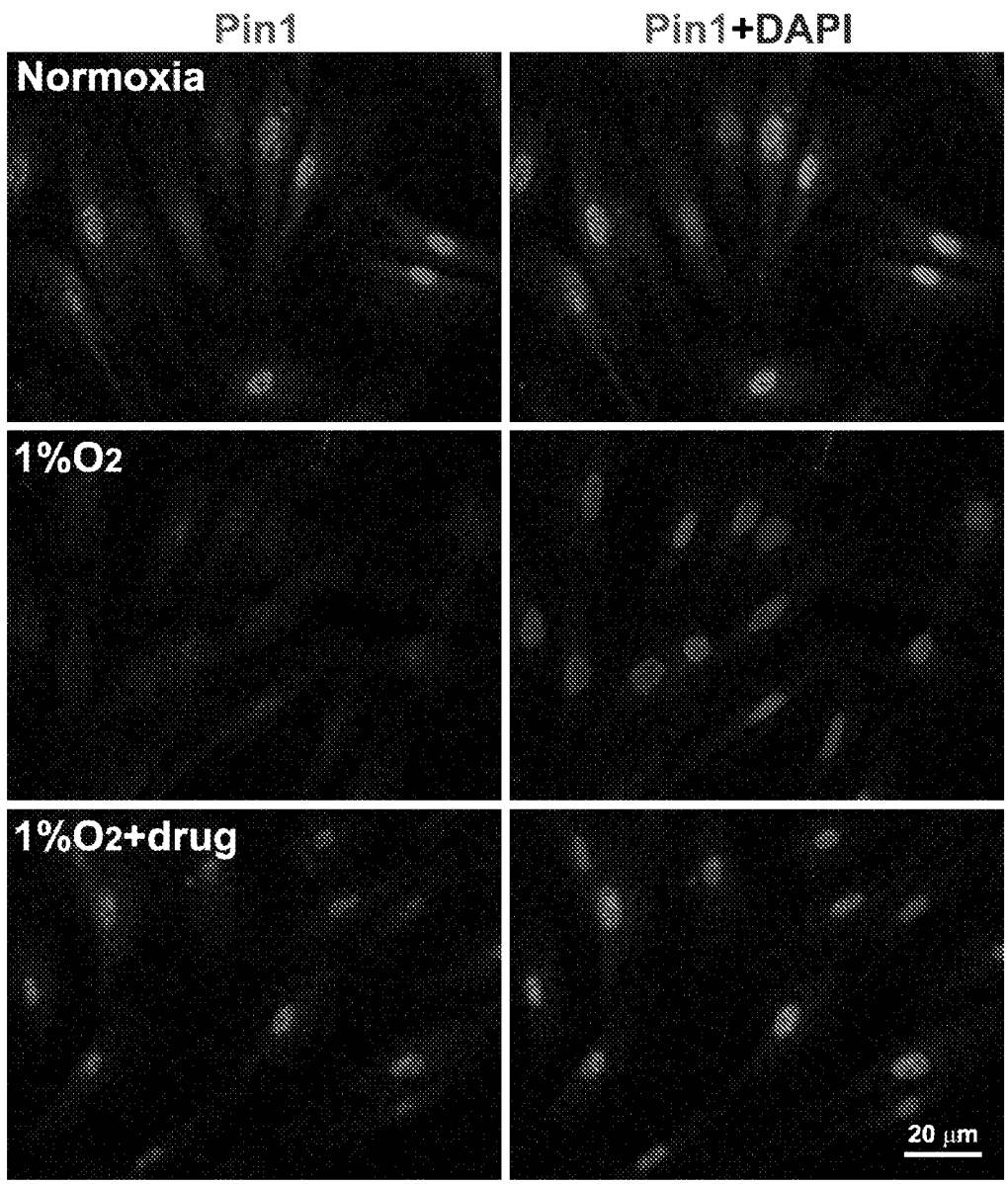
FIG. 10 depicts how hypoxia decreases Pin1 expression in the nuclei and blockade by trehalose treatment in primary trophoblasts.

Example 5: Trehalose Inhibits Inactivation of PIN1 in Nuclei of Primary Trophoblasts Primary trophoblast cells were treated with vehicle or trehalose (50 mM), exposed to low oxygen tension (1% $O_2$) or normoxia, and fixed at 3 days. After permeabilized and blocked in PBS solution containing 1% Triton-X, 3% BSA and normal donkey serum for 30 min, cells were immunostained for cis-P-tau with mouse anti-Pin1 antibody and then with Alexa Fluor 488 donkey anti-mouse secondary antibody. Cells were then mounted in anti-quench mounting medium with DAPI. As shown in FIG. 10, hypoxia decreased Pin1 expression in the nuclei of primary trophoblasts. However, trehalose blocked hypoxia-induced downregulation of nuclear Pin expression.

Figure 11:
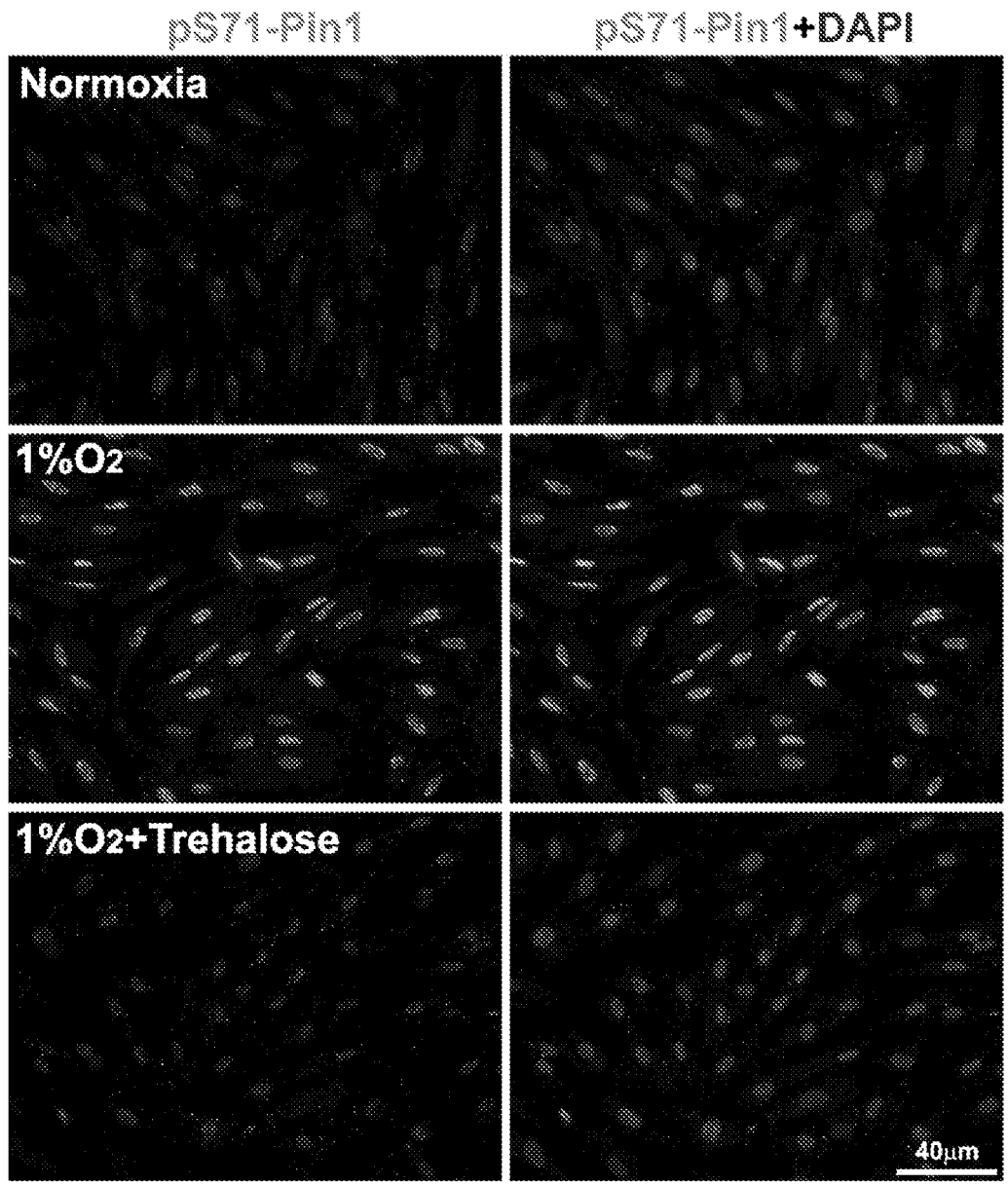
FIG. 11 depicts how hypoxia increases pS71-Pin1 expression in the nuclei which is blocked by trehalose treatment in primary trophoblasts.
Figure 12:
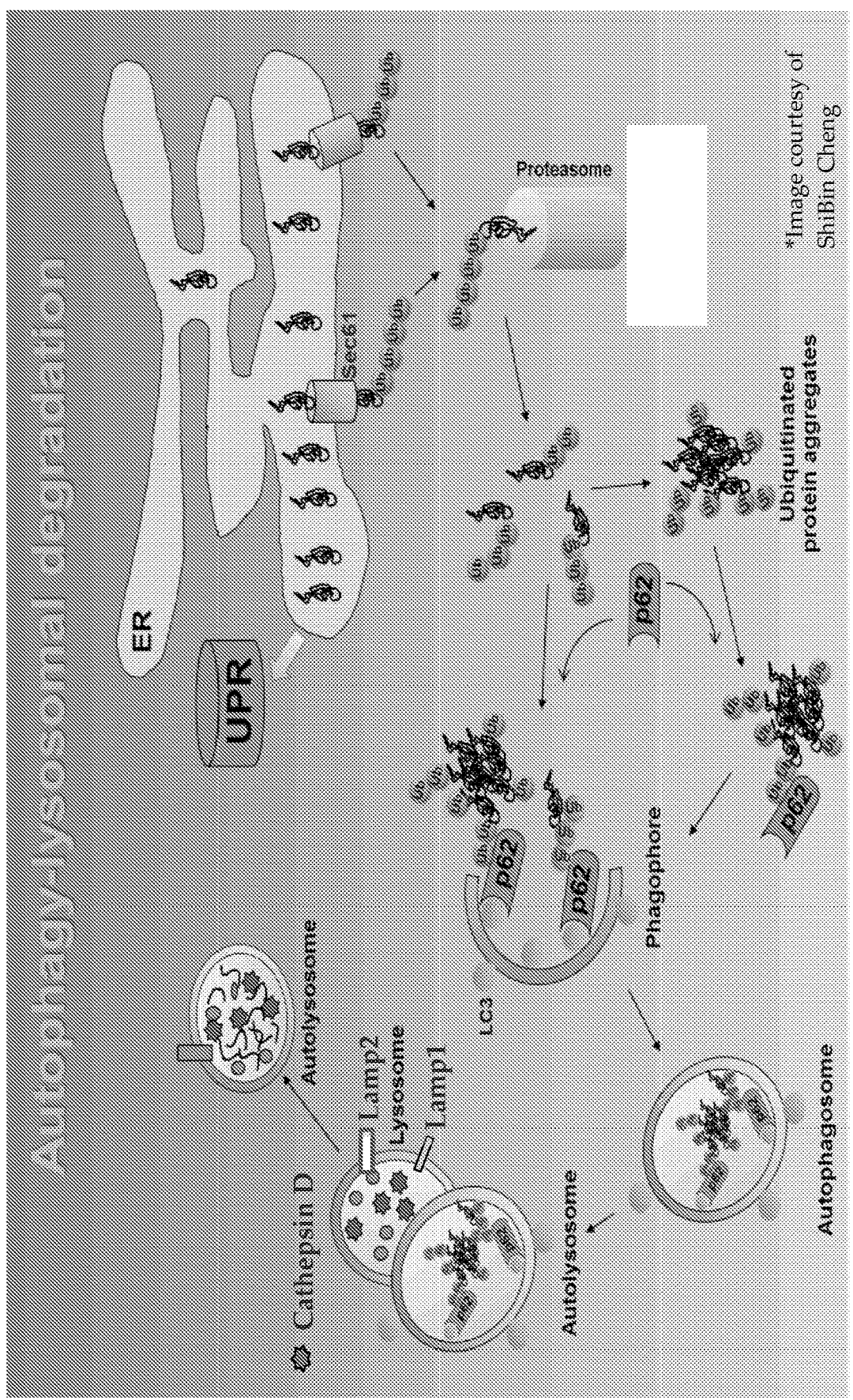
FIG. 12 is a cartoon depicting the hypothesized mechanisms for the restoration of autophagy for degradation of protein aggregates by trehalose.

Example 6: Trehalose Inhibits pS71-PIN1 Expression in Nuclei of Primary Trophoblasts Primary trophoblast cells were treated with vehicle or trehalose (50 mM), exposed to low oxygen tension (1% $O_2$) or normoxia, and fixed at 3 days. After permeabilized and blocked in PBS solution containing 1% Triton-X, 3% BSA and normal donkey serum for 30 min, cells were immunostained for pS71-Pin1 with rabbit anti-pS71-Pin1 antibody and then with Alexa Fluor 488 donkey anti-rabbit secondary antibody. Cells were then mounted in anti-quench mounting medium with DAPI. As shown in FIG. 11, hypoxia increased pS71-Pin1 expression in the nuclei of primary trophoblasts. However, trehalose inhibited hypoxia-induced upregulation of nuclear pS71-Pin1 expression.

Figure 13:
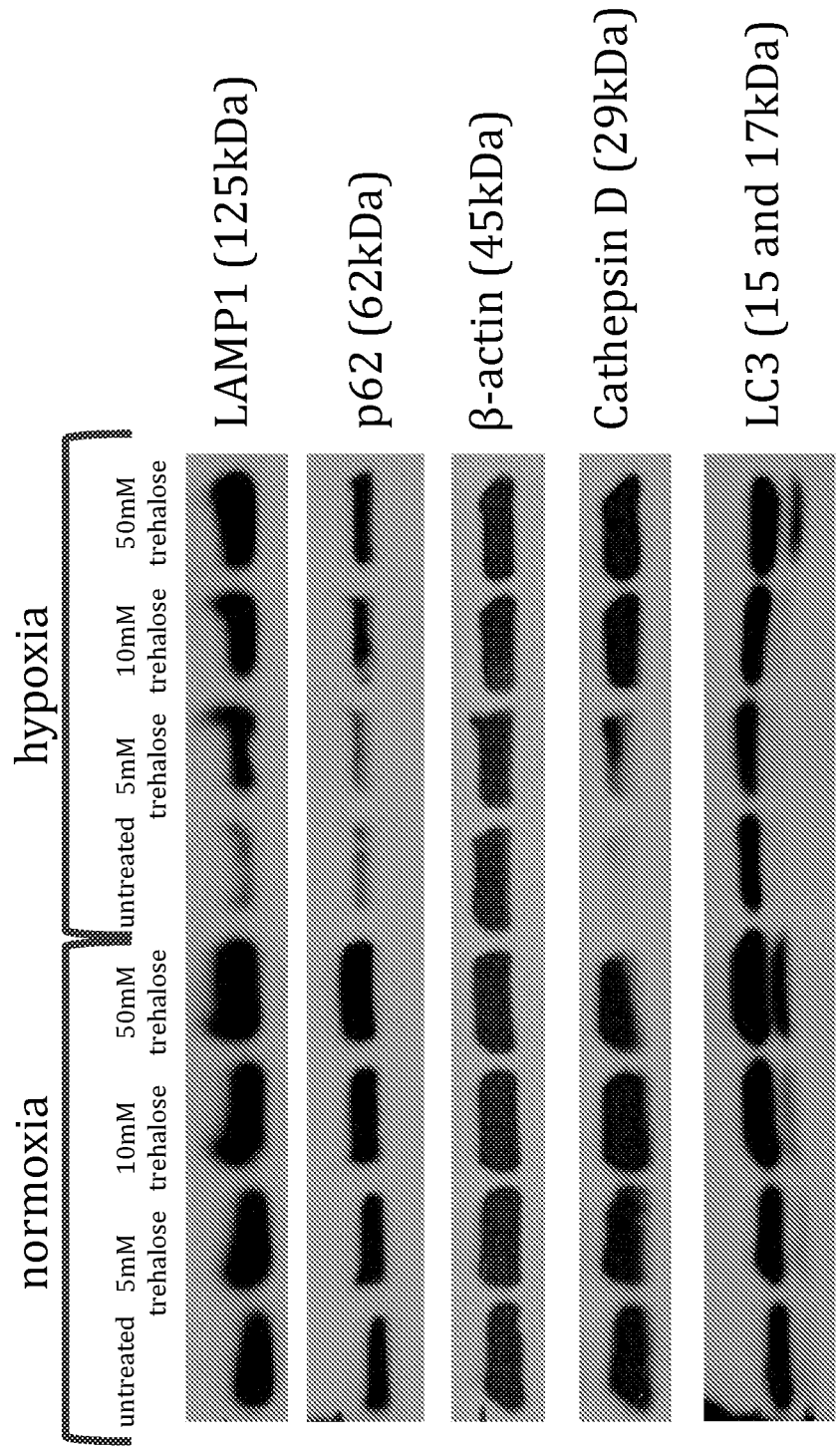
FIG. 13 depicts the restoration of autophagy markers in trehalose-treated primary trophoblast cells.

Example 7: Restoration of Autophagy Markers in Trehalose-Treated Primary Trophoblasts Primary trophoblast cells were treated with vehicle or trehalose (50 mM), exposed to low oxygen tension (1% $O_2$) or normoxia, and fixed at 3 days. Cells were harvested and lysed in RIPA lysis buffer containing protease inhibitors cocktail (Sigma). Proteins were separated by 4-12% SDS-PAGE and transferred into PVDF membrane. After blocking with 5% nonfat milk in PBS-tween (PBS-T) buffer for 30 min, the transferred membrane was incubated overnight in indicated primary antibodies, diluted in 3% or 5% BSA in PBS-T buffer, at 4° C. The membrane was washed three times, incubated for 1 h at room temperature with HRP-conjugated goat anti-rabbit/mouse IgG (Cell signaling), and then treated with enhanced chemiluminescent substrate (Thermofisher) and exposed on film. As shown in FIG. 13, hypoxia decreased indicated components of autophagy-lysosomal machinery in primary trophoblast cells. However, trehalose blocked hypoxia-induced downregulation of these proteins.

Example 8

Figure 14:
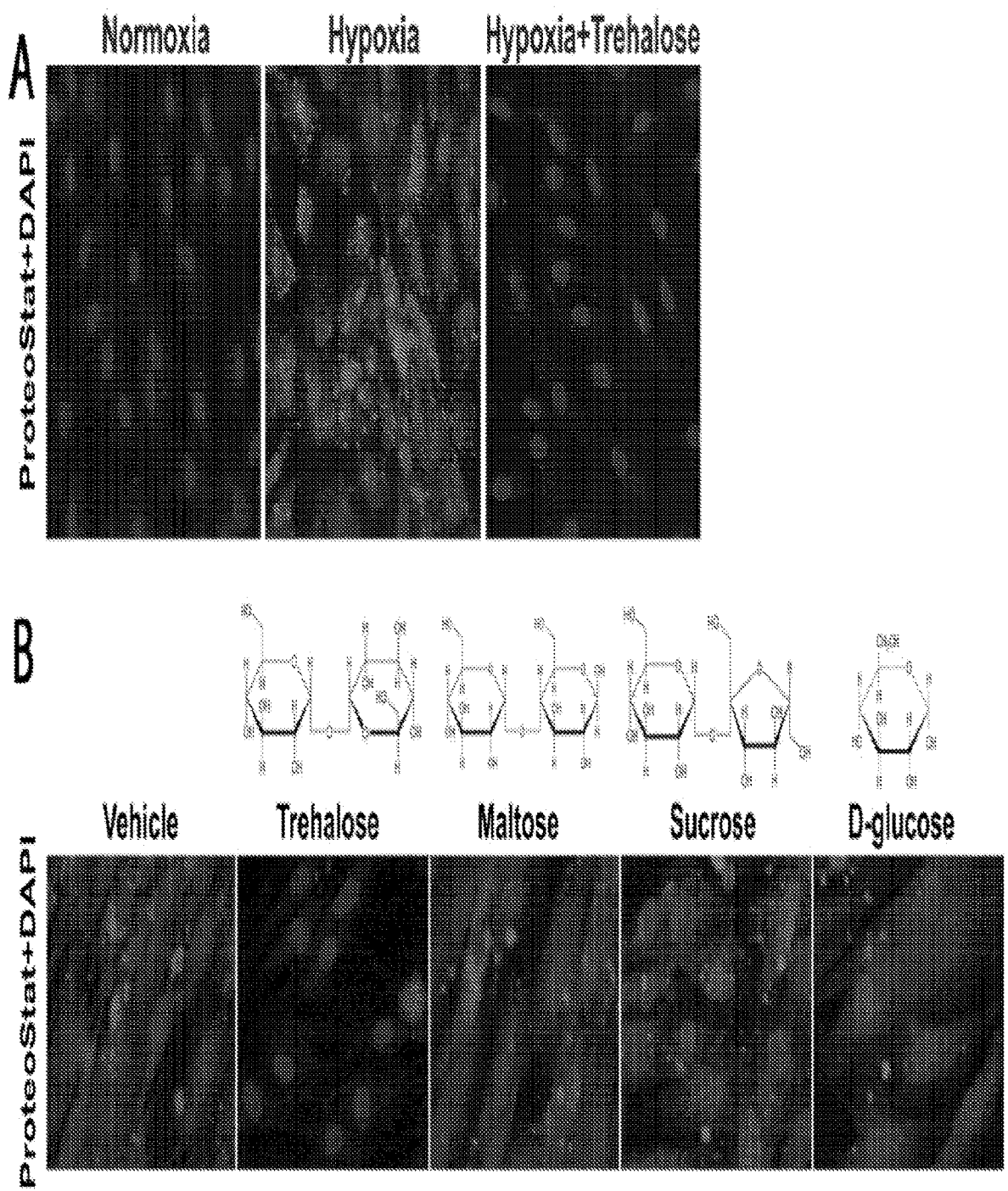
FIGS. 14A and 14B show that trehalose, but not other saccharides, inhibits protein aggregation in hypoxia-exposed primary human trophoblast cells.

FIG. 14. The effect of Trehalose on protein aggregation was examined in primary trophoblast cells in response to hypoxia, a useful cellular model of PE. Primary trophoblast cells were cultured under normoxic and hypoxic (1% $O_2$) culture conditions for 3 days, treated with vehicle, Trehalose, maltose, sucrose or D-glucose and then fixed for staining or lysed for Western blotting. ProteoStat, a dye with high affinity to aggregated proteins, was used to detect protein aggregates in treated and untreated cells. As shown in FIG. 14, robust ProteoStat signals were remarkably increased in hypoxia-exposed cells, indicating hypoxia induces accumulation of protein aggregates. However, Trehalose significantly rescued hypoxia-induced accumulation of protein aggregates, as evidenced by decreased levels of ProteoStat signals in hypoxia-exposed cells with Trehalose treatment.

Figures 15A, 15B:
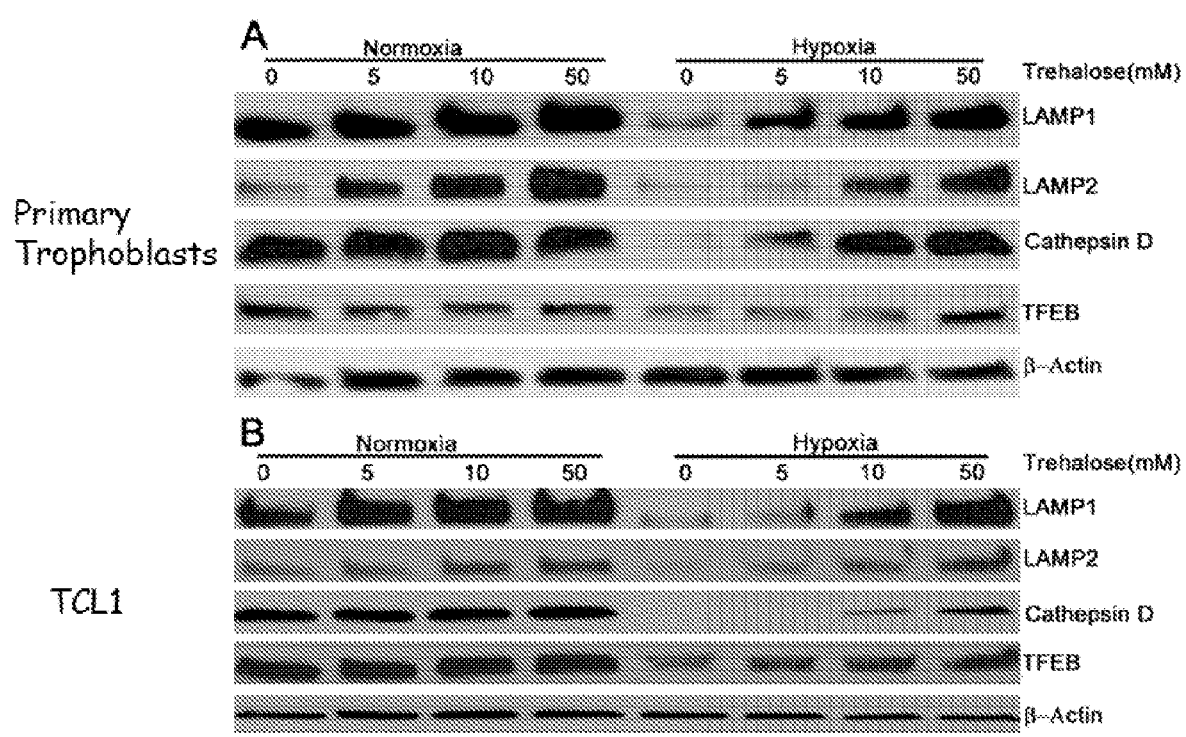
FIGS. 15A and 15B show that trehalose restores autophagy machinery (lysosomal biogenesis) in primary trophoblasts and trophoblast cell line, TCL1.

FIG. 15. To investigate the underlying mechanisms, it was evaluated whether Trehalose can enhance the activities of autophagy-lysosomal degradation pathway, the machinery responsible for clearance of protein aggregates. To this end, the signaling molecules of this machinery such as LAMP1/2, TFEB and cathepsin D were examined in primary trophoblast cells in response to hypoxia stimulation with and without Trehalose treatment. The results demonstrated that hypoxia attenuated the expression of LAMP1/2, TFEB and cathepsin D, and Trehalose significantly rescued hypoxia-induced downregulation of these molecules (FIG. 15). However, these effects were not easily observed in the cells treated with other sugars, D-glucose and maltose (data not shown). These results suggest that Trehalose, not other sugars, can rescue hypoxia-induced inhibition of autophagy-lysosomal activity, and as a result, increase clearance of aggregated proteins and prevent accumulation of aggregates as imaged in FIG. 14. Similar results were also observed in trophoblast cell line, TCL-1 (the third trimester trophoblasts).

Figure 16:
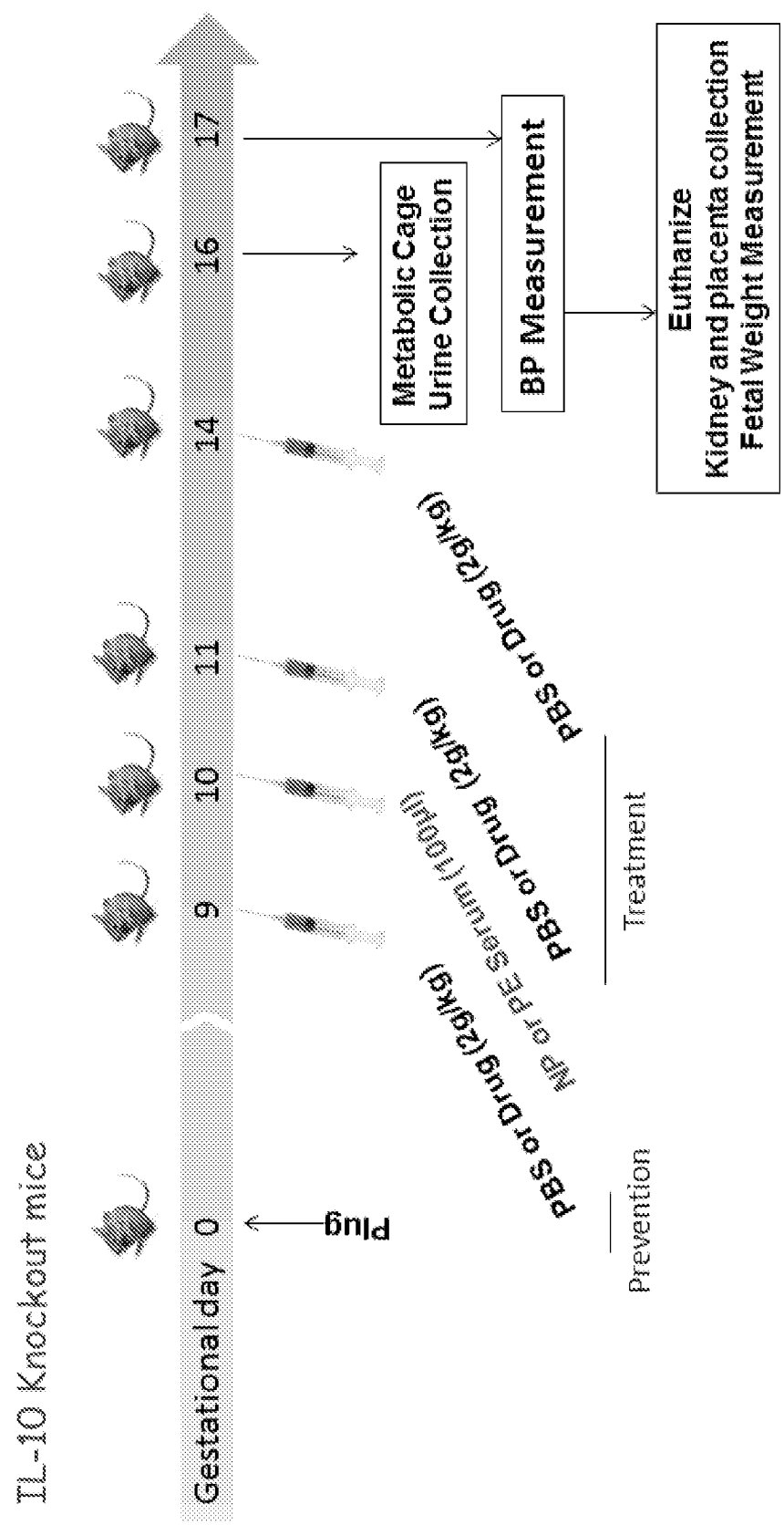
FIG. 16 depicts a schematic of the experimental approach in certain embodiments of the invention. Serum from normal pregnancy and preeclampsia injected i.p. on gestational day 10 and trehalose injected prior to after onset of preeclampsia.
Figure 18:
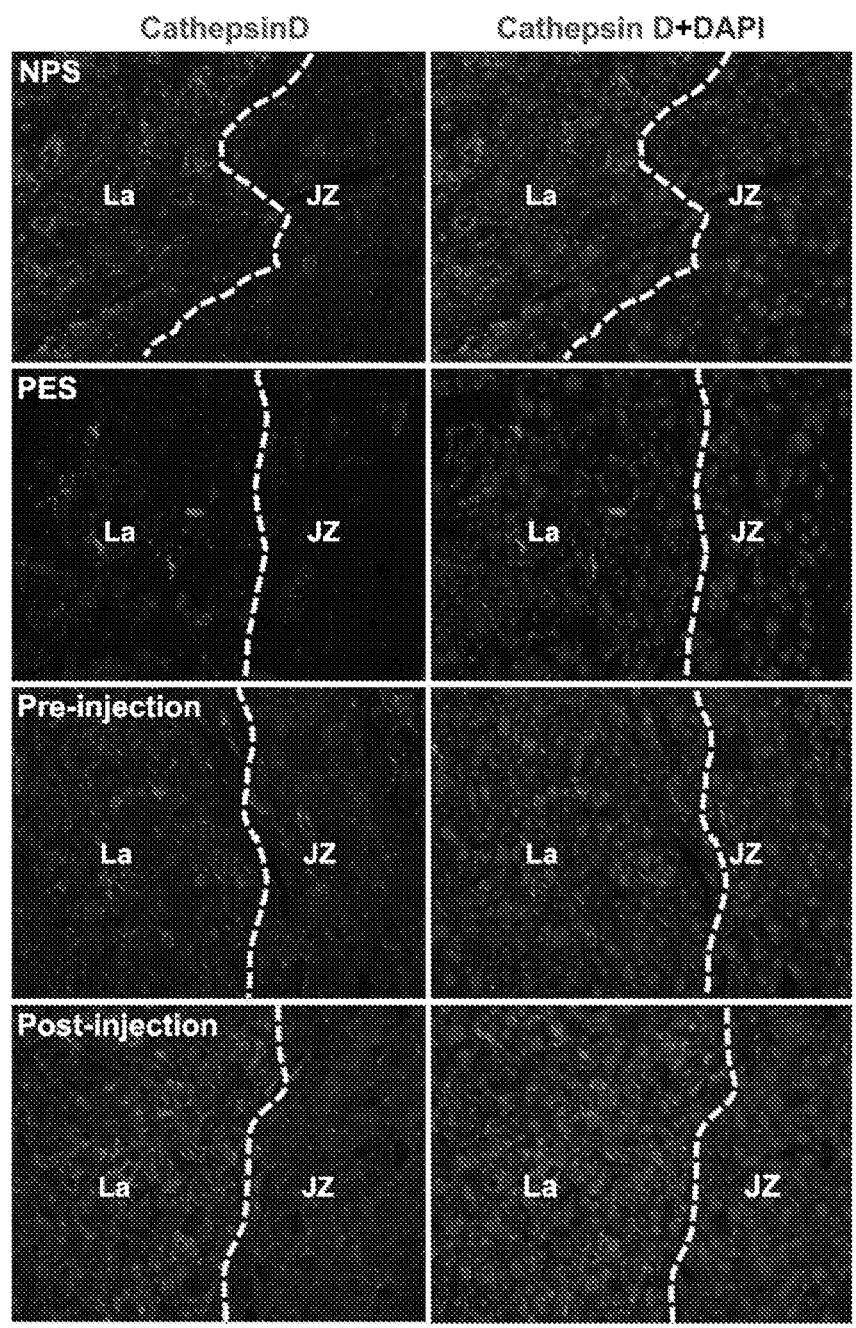
FIG. 18 shows that trehalose restores lysosomal biogenesis (autophagy) protein molecules in preeclampsia mice. NPS: normal pregnancy serum. PES: preeclampsia serum. Pre-injection: Trehalose treatment prior to induction of preeclampsia. Post-injection: Trehalose treatment after induction of preeclampsia. La represents labyrinth and JZ represents junctional zone in the mouse placenta.

FIGS. 16 and 17. Based on the results in the cellular model of PE, the effect of Trehalose treatment in an animal model of PE was evaluated next in an established mouse model of PE by a single administration of severe PE serum in pregnant IL10$^{-/-}$ mice at gd10[22]. Using this model, mice were injected intraperitoneally with vehicle, Trehalose (2 g/kg), maltose, or D-glucose (2 g/kg) at gestational day (gd) 9 (a single dose before serum injection), at gd11 and gd14 (two doses after serum injection), or at gd9, gd11 and gd14 (one dose before and two doses after serum injection) (FIG. 16). At gd17, urine was collected, blood pressure was measured, and fetal weight was recorded (FIG. 17A-D). Kidney was fixed and processed for H&E staining for glomerular endotheliosis (FIG. 17E). As reported previously, administration of severe PE sera, not normal pregnancy sera, at gd10 recapitulated a full spectrum of PE-like manifestations in IL-10$^{-/-}$ mice, including hypertension, proteinuria, renal injury and fetal growth restriction (FIG. 17). Intriguingly, Trehalose treatment with a single dose at gd9, or twice at gd11 and gd 14, or triple at gd9, gd11 and gd14 significantly reversed preeclampsia-like features including hypertension, proteinuria, growth restriction, and kidney injury (FIG. 17), although Trehalose did not have obvious effect in mice administrated with normal pregnancy sera. In contrast, maltose and de-glucose failed to rescue PE-like features in PE serum-administrated mice FIG. 18. Furthermore, the molecular events that underlie effects of Trehalose in pre-eclamptic mice were interrogated. The placentas from Trehalose-treated mice and controls were assessed for the abundance of aggregated proteins and expression of molecules in autophagy-lysosomal pathway. The results demonstrated that an increased abundance of ProteoStat signal and decreased expression of cathepsin D were detected in the labyrinth, junctional zone and decidua areas of the placenta in pre-eclamptic mice caused by severe PE sera (FIG. 18). However, Trehalose treatment with all doses significantly decreased protein aggregates and rescued the expression of cathepsin D in pre-eclamptic mice (FIG. 18).

EQUIVALENTS

Although various embodiments of the invention have been described using specific terms, such description is for illustrative purposes only, and it is to be understood that changes and variations may be made without departing from the spirit or scope of the following claims. Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto.

INCORPORATION BY REFERENCE

The entire contents of all patents, published patent applications, and other references cited herein are hereby expressly incorporated herein in their entireties by reference.

The invention claimed is:

1. A method of treating pre-eclampsia in a subject in need thereof, the method comprising administering to the subject a pharmaceutical composition comprising a therapeutically effective amount of about 2 g/kg of trehalose or a derivative or prodrug thereof, thereby treating pre-eclampsia in the subject.

2. A method of delaying the onset of or treating pre-eclampsia in a subject in need thereof, the method comprising:
    a) detecting a level of at least one tauopathy marker in a sample obtained from the subject,
    b) comparing the level of the at least one tauopathy marker to a corresponding reference level; and wherein if the level of the at least one tauopathy marker is different from the corresponding reference level,
    c) administering to the subject a pharmaceutical composition comprising a therapeutically effective amount of about 2 g/kg of trehalose or a derivative or prodrug thereof, thereby treating or delaying the onset of pre-eclampsia in the subject.

3. The method according to claim 2, wherein the sample is selected from the group consisting of a serum sample, a urine sample and a sample obtained from the placenta.

4. The method according to claim 3, wherein the sample is a serum or urine sample.

5. The method according to claim 2, wherein the at least one tauopathy marker is selected from the group consisting of a protein aggregate, cis p-tau and combinations thereof.

6. The method according to claim 1, wherein the pre-eclampsia is characterized by elevated levels of cis-p-tau in a sample obtained from the subject.

7. The method according to claim 1, wherein the pre-eclampsia is characterized by depressed levels and/or inactivation of Pin-1.

8. The method of claim 1, wherein the pre-eclampsia is characterized by the presence of protein aggregates in a sample obtained from the subject.

9. The method according to claim 1, wherein the trehalose promotes degradation of protein aggregates.

10. The method according to claim 8, wherein the sample is a serum sample or a urine sample.

11. The method according to claim 1, wherein the subject is a human female.

12. The method of claim 11, wherein the human female is characterized by a risk factor selected from the group consisting of previous history of pre-eclampsia, multiple gestation, history of chronic high blood pressure, history of diabetes, history of kidney disease, history of organ transplant, first pregnancy, obesity and combinations thereof.

13. The method of claim 1, further comprising obtaining trehalose or a derivative or prodrug thereof.

* * * * *